US010260811B2

(12) United States Patent
Rohner et al.

(10) Patent No.: US 10,260,811 B2
(45) Date of Patent: Apr. 16, 2019

(54) DENTAL FURNACE

(71) Applicant: Ivoclar Vivadent AG, Schaan (LI)

(72) Inventors: Gottfried Rohner, Altstatten (CH);
Walter Pokorny, Bludesch (AT);
Robert Grunenfelder, Vaduz (LI);
Frank Rothbrust, Frastanz (AT)

(73) Assignee: Ivoclar Vivadent AG, Schaan (LI)

( * ) Notice: Subject to any disclaimer, the term of this patent is extended or adjusted under 35 U.S.C. 154(b) by 453 days.

(21) Appl. No.: 14/994,405

(22) Filed: Jan. 13, 2016

(65) Prior Publication Data
US 2016/0195334 A1    Jul. 7, 2016

Related U.S. Application Data

(63) Continuation-in-part of application No. 14/978,486, filed on Dec. 22, 2015, now abandoned, which is a
(Continued)

(51) Int. Cl.
*F27B 17/02* (2006.01)
*A61C 13/20* (2006.01)
(Continued)

(52) U.S. Cl.
CPC .............. *F27B 17/025* (2013.01); *A61C 5/77* (2017.02); *A61C 13/20* (2013.01); *A61C 13/0006* (2013.01); *A61C 13/12* (2013.01)

(58) Field of Classification Search
CPC ... A61C 5/10; A61C 13/0003; A61C 13/0006; A61C 13/20; A61C 5/77; A61C 13/12; F27B 17/025; F27B 5/10; H05B 3/00
(Continued)

(56) References Cited

U.S. PATENT DOCUMENTS 4,139,341 A * 2/1979 Pfaffenbauer ........... F27B 17/02
432/184
4,370,878 A 2/1983 Carrieri
(Continued)

FOREIGN PATENT DOCUMENTS

DE       8202852.4 U1    6/1982
DE        8208852 U     10/1982
(Continued)

OTHER PUBLICATIONS

Dekema, Dental Furnace AUSTROMAT 3001 Manual, Version 01/2005, pp. 4-5 and 10-15.
(Continued)

*Primary Examiner* — Jimmy Chou
(74) *Attorney, Agent, or Firm* — Ann M. Knab; Thad McMurray

(57) ABSTRACT

The invention relates to a dental furnace wherein a firing chamber is heated up in a first heating-up period at a first heating-up rate of more than 501 K/min, in particular more than 1001 K/min, which heats the furnace to at least 10001 C., in particular to 1100-12501 C. The first heating-up period is followed by an intermediate heating period, which is at least five minutes long, in particular at least ten minutes long, the gradient or heating-up rate of which is adapted to the material to be sintered in the dental furnace (10), and wherein this is followed by an end heating-up period (44) during which heating up is effected at a heating-up rate of more than 301 K/min, in particular approximately 501 K/min, and wherein during this the furnace temperature is held for at least five minutes, in particular for at least 25 minutes, above the temperature toward the end of the first heating-up period, and wherein forced cooling of the furnace (10) is performed after this.

19 Claims, 5 Drawing Sheets

Related U.S. Application Data continuation-in-part of application No. 14/684,535, filed on Apr. 13, 2015, now Pat. No. 9,557,114, which is a continuation of application No. 12/380,905, filed on Mar. 5, 2009, now Pat. No. 9,033,703.

(51) Int. Cl.
*A61C 5/77* (2017.01)
*A61C 13/00* (2006.01)
*A61C 13/12* (2006.01)

(58) Field of Classification Search
USPC .............. 431/1, 32, 49, 930; 433/32, 61, 62; 219/425
See application file for complete search history.

(56) References Cited

U.S. PATENT DOCUMENTS

| | | | | |
|---|---|---|---|---|
| 4,547,327 A * | 10/1985 | Bruins | A61K 6/08 | 264/112 |
| 4,970,050 A | 11/1990 | Groll et al. | | |
| 5,045,765 A * | 9/1991 | Wissler | B60H 1/00742 | 296/223 |
| 5,072,360 A | 12/1991 | Knorpp et al. | | |
| 5,775,912 A | 7/1998 | Panzera et al. | | |
| 5,788,485 A * | 8/1998 | Grunenfelder | A61C 13/20 | 432/206 |
| 5,788,498 A * | 8/1998 | Wohlwend | A61C 13/0003 | 264/19 |
| 5,905,937 A * | 5/1999 | Plucknett | B22F 3/1017 | 419/12 |
| 5,948,342 A * | 9/1999 | Nakazawa | B29C 64/153 | 264/113 |
| 5,997,293 A * | 12/1999 | Grunenfelder | F27B 17/025 | 432/206 |
| 6,025,065 A | 2/2000 | Claussen et al. | | |
| 6,126,895 A | 10/2000 | Dennis et al. | | |
| 6,252,202 B1 * | 6/2001 | Zychek | F27B 17/025 | 219/385 |
| 6,811,396 B2 * | 11/2004 | Sudau | B21B 1/466 | 266/103 |
| 6,835,066 B2 * | 12/2004 | Iiyama | A61C 5/77 | 433/215 |
| 7,020,539 B1 * | 3/2006 | Kovacevic | B22F 3/1055 | 483/16 |
| 7,084,870 B2 * | 8/2006 | Fang | H04R 25/652 | 345/420 |
| 7,092,780 B2 * | 8/2006 | Ganley | A61C 13/0004 | 700/117 |
| 7,236,842 B2 * | 6/2007 | Kopelman | A61C 13/0004 | 700/98 |
| 8,317,512 B2 * | 11/2012 | Jussel | A61C 13/20 | 110/190 |
| 2002/0029094 A1 * | 3/2002 | Koreishi | B29C 64/153 | 700/197 |
| 2002/0106611 A1 | 8/2002 | Bhaduri et al. | | |
| 2003/0183612 A1 * | 10/2003 | Timans | C30B 31/12 | 219/390 |
| 2004/0050905 A1 * | 3/2004 | Endo | B23K 1/005 | 228/101 |
| 2004/0106087 A1 * | 6/2004 | Weigl | A61C 13/0004 | 433/218 |
| 2004/0245663 A1 * | 12/2004 | MacDougald | A61C 13/0003 | 264/16 |
| 2005/0098064 A1 * | 5/2005 | Schweiger | C03C 10/0027 | 106/35 |
| 2005/0117145 A1 * | 6/2005 | Altman | G01N 21/87 | 356/30 |
| 2005/0201795 A1 | 9/2005 | Kawachi et al. | | |
| 2005/0250067 A1 * | 11/2005 | Rohner | F27B 17/025 | 432/159 |
| 2005/0261795 A1 * | 11/2005 | Ghosh | A61C 13/0004 | 700/118 |
| 2006/0030165 A1 * | 2/2006 | Ingle | H01L 21/02164 | 438/795 |
| 2006/0088077 A1 * | 4/2006 | Jussel | A61C 13/20 | 374/141 |
| 2006/0089977 A1 * | 4/2006 | Cramer | H04L 29/06 | 709/218 |
| 2006/0191916 A1 | 8/2006 | Stephan et al. | | |
| 2006/0261503 A1 * | 11/2006 | Sago | A61C 13/0003 | 264/16 |
| 2007/0023971 A1 * | 2/2007 | Saha | A61C 13/203 | 264/432 |
| 2007/0190492 A1 * | 8/2007 | Schmitt | A61C 13/0004 | 433/213 |
| 2007/0203600 A1 * | 8/2007 | Shibata | A61C 13/0004 | 700/98 |
| 2007/0275352 A1 * | 11/2007 | Gubler | A61C 13/0004 | 433/201.1 |
| 2008/0015727 A1 * | 1/2008 | Dunne | A61B 5/4547 | 700/118 |
| 2008/0213611 A1 | 9/2008 | Asgari | | |
| 2008/0237211 A1 * | 10/2008 | Jussel | A61C 13/20 | 219/390 |
| 2008/0261165 A1 * | 10/2008 | Steingart | A61C 13/0004 | 433/24 |
| 2009/0194527 A1 * | 8/2009 | Okada | H05B 6/1263 | 219/624 |
| 2009/0276070 A1 * | 11/2009 | Burkes | B23P 15/00 | 700/98 |
| 2009/0287332 A1 * | 11/2009 | Adusumilli | A61C 13/0004 | 700/98 |
| 2009/0306801 A1 * | 12/2009 | Sivak | A61F 5/0111 | 700/98 |
| 2010/0028835 A1 * | 2/2010 | Hansen | A61C 13/083 | 433/218 |
| 2010/0028836 A1 * | 2/2010 | Gubler | A61C 13/0004 | 433/223 |
| 2010/0047731 A1 * | 2/2010 | Zubler | A61C 13/20 | 432/45 |
| 2010/0058588 A1 * | 3/2010 | Heinz | A61C 3/02 | 29/896.1 |
| 2010/0143868 A1 * | 6/2010 | Hintersehr | A61C 13/0004 | 433/172 |
| 2011/0147968 A1 * | 6/2011 | Zubler | A61C 13/20 | 264/16 |
| 2011/0309540 A1 * | 12/2011 | Dittmann | F27D 5/0043 | 264/16 |

FOREIGN PATENT DOCUMENTS

| | | |
|---|---|---|
| DE | 3841902 C1 | 11/1989 |
| DE | 3831539 A1 | 3/1990 |
| DE | 3831539 C3 | 3/1990 |
| DE | 19753837 A1 | 6/1999 |
| DE | 69902570 T2 | 4/2003 |
| EP | 0337897 A1 | 10/1989 |
| EP | 0985893 B1 | 8/2002 |
| JP | 2-116366 A | 1/1990 |
| JP | 06-121800 A | 5/1994 |
| JP | 06-269466 A | 9/1994 |
| JP | 7-32787 B | 4/1995 |
| JP | 10-033564 A | 2/1998 |
| JP | 10-075964 A | 3/1998 |
| JP | 2000-329477 A | 11/2000 |

OTHER PUBLICATIONS

Dekema, Dental Furnace AUSTROMAT D4 Manual, Version 08/2005, 99. 4-5, 21-23, and 28-33.

Dekema, Dental Furnace AUSTROMAT 3001 press-i-dent Manual, Version 01/2005, pp. 4-5 and 10-16.

Dekema, Technical drawing of the combustion chamber insulation of AUSTROMAT 3001, 1 page.

Dekema, Order confirmation for RATH company of AUSTROMAT 3001 and Safety Data Sheet, 11 pages.

Dekema, Notice of Opposition filed in DE 10 2008 012 578.4, 13 pages.

(56) References Cited

OTHER PUBLICATIONS

Menezes, R.R. et al., Microwave hybrid fast sintering of porcelain bodies, Journal of Materials Processing Technology, May 2007, vol. 190, pp. 223-229.
Agarwal, G., et al., Microstructural development of ZnO using rate-controlled sintering dilatometer, Journal of Materials Research, Mar. 1996, vol. 11, No. 3, pp. 671-679.
Programat P300, Operating Instructions, Ivoclar Vivadent AG, version 2, Mar. 2006, pp. 1-34.
"Alumina-silica paper" http://www.zrci.com/aspa.htm.
http://web.archive.org/web/20010213232049/http://www.zrci.com/aspa.htm.

* cited by examiner

DENTAL FURNACE

CROSS-REFERENCE TO RELATED APPLICATIONS

This present application claims priority to and is a continuation-in part of U.S. application Ser. No. 14/978,486, filed on Dec. 22, 2015, which is a continuation-in-part application of U.S. application Ser. No. 14/684,535, filed on Apr. 13, 2015, which claims priority to and is a continuation application of U.S. application Ser. No. 12/380,905, filed Mar. 5, 2009, which claims foreign priority benefits under 35 U.S.C. § 119(a)-(d) from German patent application ser. no. 10 2008 012 578.4 filed Mar. 5, 2008, all of which are hereby incorporated by reference in their entirety.

TECHNICAL FIELD

The invention relates to a dental furnace which is heated up in stages and also cooled down to a method for heating up and cooling down, and more particularly to such a furnace used for sintering dental materials.

BACKGROUND OF THE INVENTION

A dental furnace of this type and a method of this type have long been known. Precisely for sintering adapted dental materials it is important to cause the heating up, the actual firing, and indeed the cooling down as well, to proceed according to a predetermined and reproducible scheme in order on the one hand to ensure the required material compaction, but on the other hand also to ensure that the shrinkage takes place uniformly to the entire extent.

For this purpose, the temperature in the interior of the dental furnace is typically controlled with a precisely determined temperature profile. For this purpose, the heating elements are connected to a corresponding control device, and a temperature sensor is normally used.

The temperature sensor is typically arranged in the upper region of the firing chamber serving as working space, the restorations being placed there.

Temperature sensors can therefore be arranged in or on the wall of the firing space, and it is known to use special calibration devices to ensure that the temperature in the interior of the dental furnace follows a predetermined temperature profile.

On the other hand, the heat capacity of the introduced mass is a parameter that influences the heating-up profile of the dental material. The heating-up rate is typically lower if large masses are used, and higher if small masses are used. In order to compensate for this effect, it is possible to detect the introduced mass beforehand and to provide calibration curves for different masses. However, this is complicated and greatly dependent on the operator's care.

Moreover, the mass of the introduced dental material cannot usually be ascertained exactly.

Therefore, it is known to work with a comparatively low heating-up rate in order to provide for the dental materials the possibility of bringing about a homogeneous temperature compensation, irrespective of what mass is present. Although this method is good in principle, it is diametrically opposite to the desires in the dental laboratory to save costs by means of a short production cycle.

Furthermore, U.S. Pat. No. 6,025,065 has, however, also disclosed combining an extremely high heating-up rate of more than 100° C./min with a high temperature of 1300° C. to 1600° C. Although the sintering furnace therein is in principle extremely well suited to the rapid sintering of materials, the dimensional accuracy thereof is of lesser relevance. Such a furnace is not suitable, however, for dental materials.

OBJECTS AND SUMMARY OF THE INVENTION

Against this background, the invention is based on the object of providing a dental furnace which are particularly well suited to the production of dental materials.

The invention provides for heating up a dental furnace with a firing chamber at an extremely high first heating-up rate until a temperature corresponding to a presintering temperature has been reached. What can be achieved by means of the presintering expedient according to the invention is that the sintering material can be processed after the presintering.

Surprisingly, by means of the rapid heating up according to the invention at the first high heating-up rate, which is ended only at a temperature of 1000° C., 1100° C. or even 1200° C., the sintering cycle can be significantly accelerated without disadvantages occurring in the case of the final strength, on the one hand, or in the case of the accuracy of fit, on the other hand.

Surprisingly, the observation even becomes apparent that the final strength is increased by this rapid heating up in comparison with a slower heating up.

According to the invention, the first heating up with the high first heating-up period is followed by an intermediate heating period, the heating-up rate or temperature gradient of which is significantly smaller than that of the initial heating-up period. By way of example, the temperature gradient during the intermediate heating period can be 2° K, 3° K, 5° K or 10° K/min.

After the intermediate heating period, the duration of which can be adapted to the requirements in wide ranges and can be for example 5 min, 10 min, 20 min or 30 min, an end heating-up period is provided, the temperature gradient or heating-up rate of which is likewise significantly higher and can be for example at least 20° K/min, but preferably approximately 50° K/min.

The temperature difference between the temperature toward the end of the intermediate heating period and the end temperature toward the end of the end heating-up period is comparatively small and is for example somewhat more than 100°, or 200° for example, without any deterioration in the accuracy of fit.

By contrast, the accuracy of fit is significantly improved by the low heating-up rate during the intermediate heating period.

According to the invention it is particularly expedient for the end of the heating-up period to be followed by a holding period, during which the temperature in the firing chamber is held substantially at the end temperature toward the end of the heating-up period or just below that. The final density and the strength of the dental material can be significantly improved by this measure.

The realization of a particular dental furnace is particularly expedient for the configuration of the temperature profile according to the invention. In order to be able to realize the high temperature gradient desired, a dental furnace according to the invention preferably has a low heat capacity between the heating elements and the firing space, which heat capacity may be composed for example of a rather thin insulation material, for example quartz glass. The comparatively effective heating elements would permit the dental furnace to be heated up to 1600° C. from room temperature within somewhat more than 10 min, where it is understood that a particular temperature profile is sought according to the invention.

The dental furnace according to the invention takes account particularly of the fact that the sintering in the case of the dry sintering takes place in three stages, namely an initial stage, an intermediate stage and an end stage, wherein the sintering rate, that is to say the contraction of the material per unit time, is the highest in the intermediate stage, such that for example 90% of the final density can be achieved at the end of the intermediate stage.

According to the invention it is preferred to allow the initial stage to be undergone as early as during the presintering, such that the sintering rate during sintering to completion only undergoes the intermediate and end stages.

In this connection it is expedient according to the invention if a low heat capacity is also used for the thermal insulation, wherein it is also possible, for example, to keep the thermal insulation layer at a distance from the heating element, such that the capacity no longer plays a part. This additionally has the particular advantage that the cooling down of the heating elements can be significantly improved by convection. By way of example, it is also possible to realize rear-ventilated heating elements, that is to say heating elements in which the air flow with the furnace hood open also contributes to the cooling of the heating elements from the side remote from the firing chamber.

The dental furnace according to the invention can be a furnace with a firing chamber which can be removed from a substructure. In this case, either a lifting mount or a pivoting mount or a combination of these mounts is possible. One example of such a mount can be seen from U.S. Pat. No. 5,788,485.

In addition to the convection cooling it is also possible to use active cooling by means of a fan in order in this respect in any case to achieve the desired cooling-down rate. This holds true particularly when a dental furnace in a traditional form with a firing chamber door is used, a dental firing furnace with a flat bearing surface and a removable firing hood being preferred.

According to the invention, the temperature and duration of the precompaction, by means of the presintering, can be adapted to the requirements within wide ranges. The presintering is preferably effected in a separate process step beforehand on the dental block. By way of example, the presintering can be effected at the final temperature of the first heating-up period, that is to say for example at 1100° C. or at 1250° C. This presintering has the advantage that the presintered material can still be mechanically processed since the hardness is significantly lower than in the material sintered to completion.

By comparison with high-temperature sintering furnaces known per se, it is particularly preferred according to the invention that the cycle time is significantly reduced, by comparison with the typical 8 to 10 hours for sintering to completion and cooling down in the case of known high-temperature sintering furnaces.

According to the invention, it is possible, by contrast, to reduce the total cycle time to less than three hours, including the cooling down, and in a modified embodiment of the solution according to the invention, the total cycle time can be reduced to less than 90 min despite the use of high-strength dental ceramic with firing temperatures of more than 1500° C.

An alternative embodiment provides for using, instead of a sintering furnace, a microwave furnace for the realization of the dental furnace according to the invention.

The firing curve accelerated according to the invention is distinguished in diagrammatic representation by a "block form with shoulders". The first heating-up period is extremely short with a large temperature gradient, as is the end cooling-down phase with a likewise steep temperature gradient. A temperature phase above 1100° C. that is significantly lengthened in comparison with the total length of the heating curve is thus available, which can then be optimized according to the invention. Thus, it is expedient according to the invention if the "high-temperature phase" takes up 68%, that is to say in this respect just below 70%, of the total firing cycle in the case of a short firing curve of less than three hours, and even above 80% in the case of a standard firing curve, in each case relative to the heating up from room temperature and the cooling down to room temperature and the duration for which the firing temperature of more than 1100° C. is complied with.

By obviating kiln furniture, it is possible to further reduce the heat capacity or thermal mass in relation to kilns having kiln furniture. It is also particularly expedient according to the invention if, instead of passive cooling, active cooling is also effected precisely in the interspace between the thermal insulation and the heating element, and also within the open firing space, such that the desired cooling-down rate can be achieved.

It is preferred in this connection if in this respect rear-ventilated firing chamber is embodied expediently in terms of flow, such that the active ventilation can be realized with a comparatively low fan rotational speed and thus very quietly.

For this purpose, two flow ducts are preferably provided, namely a rear-ventilation flow duct and a flow duct through the firing chamber, wherein it is understood that the convection cooling can also be produced at least in part—precisely at high temperatures.

In a further preferred configuration it is provided that the sintering material to be sintered is heated up in a first heating-up period at a heating-up rate of more than 50° K/min, wherein, between the end of the first heating-up period and the beginning of an end heating period there is an intermediate heating period at a heating-up rate significantly lower than 50° K/min, in particular less than 10° K/min, and wherein the first heating-up period and the end heating period are set in a material-independent manner, and wherein the intermediate heating period is defined, with regard to its length and its heating-up rate, in a manner dependent on the material to be sintered.

In a further preferred configuration it is provided that the maximum temperature in the heating chamber is approximately 1600° C. and the furnace can be heated up to 1600° C. proceeding from room temperature in its heating chamber, within less than 30 minutes.

In a further preferred configuration it is provided that the intermediate heating-up rate is lower than the initial heating-up rate by approximately a power of 10, in particular by a factor of 10 to 50.

In a further preferred configuration it is provided that a heating chamber of the furnace is surrounded by a heat-resistant insulation, in particular a pressed shaped part composed of fiber, the wall thickness of which is preferably between 15 and 25 mm.

In a further preferred configuration it is provided that the intermediate heating period is chosen in terms of the temperature and/or the time such that it covers the intermediate stage of the sintering process of the dental material to be sintered, in which the sintering rate, plotted against the temperature/time, is the highest.

In a further preferred configuration it is provided that the dental material to be fired is presintered and/or precompacted and prior to the actual sintering has a strength which is significantly lower than, in particular less than half the magnitude of, the final strength of the sintering material.

In a further preferred configuration it is provided that the initial heating-up rate is chosen such that it corresponds to the maximum heating-up rate at which no overshoot arises upon the transition from the initial heating-up period to the intermediate period, but is at least 50° K min$^{-1}$.

In a further preferred configuration it is provided that, after a holding time has elapsed, the furnace cools down at a first cooling-down rate, which is less than the heating-up rate of the initial heating-up period and greater than the heating-up rate of the intermediate heating-up period, and wherein a higher, second cooling-down rate is set after this.

In a further preferred configuration it is provided that the dental furnace is a microwave furnace.

In a further preferred configuration it is provided that a method wherein a heating chamber is heated up in a first heating-up period at a first heating-up rate of more than 50° K/min, in particular approximately 100° K/min, which heats up the furnace to at least 1000° C., in particular to 1100° C. to 1250° C., wherein the first heating-up period is followed by an intermediate heating period, which is at least five minutes long, in particular at least ten minutes long where the gradient or heating-up rate thereof is subsequently adapted to the material to be sintered in the furnace, and wherein this is followed by an end heating-up period, during which heating up is effected at a heating-up rate of more than 20° K/min, in particular approximately 50° K/min, and wherein during this the furnace temperature is held for at least five minutes, in particular for 25 minutes, above the temperature toward the end of the first heating-up period, and wherein forced cooling of the furnace is performed after this.

In a further preferred configuration it is provided that a method wherein the sintering material to be sintered is heated up in a first heating-up period at a heating-up rate of more than 50° K/min, wherein, between the end of the first heating-up period and the beginning of an end heating period, preheating is effected for an intermediate heating period at a heating-up rate significantly lower than 50° K/min, in particular less than 10° K/min, and wherein the first heating-up period and the end heating period have been or are set in an object-independent manner, and wherein the intermediate heating period is defined, with regard to its length and its heating-up rate, in a manner dependent on the material to be sintered.

In a further preferred configuration it is provided that dental tooth replacement material is sintered in dry fashion or in liquid sintering, wherein the sintering material comprises an oxide ceramic which is composed, in particular, of $ZrO_2$, of $Al_2O_3$ and compositions thereof and comprises, in particular, a doping auxiliary.

In a further preferred configuration it is provided that, starting when the holding time has elapsed, forced cooling of the furnace is performed, which leads to the cooling down of the tooth replacement material to a removal temperature, in particular of approximately 400° C., in less than 60 minutes, in particular 20 to 60 minutes.

Further advantages, details and features will become apparent from the description below of an exemplary embodiment with reference to the drawing, in which:

DETAILED DESCRIPTION

Figure 1:
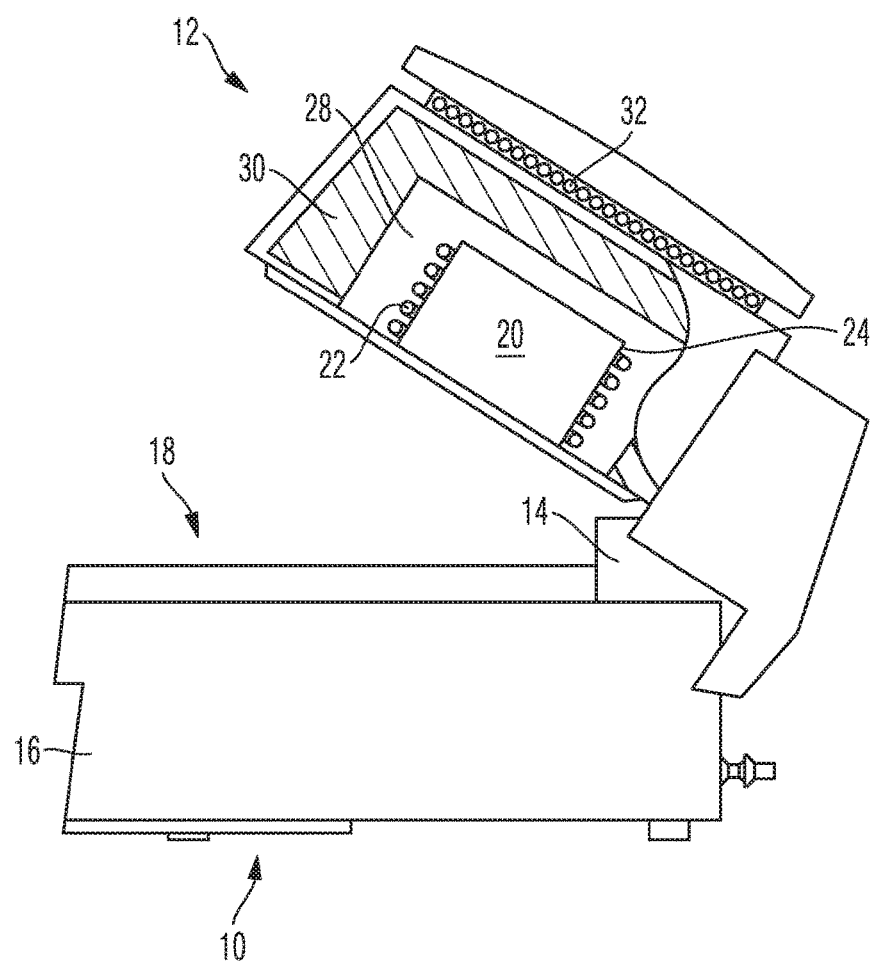
FIG. 1 shows a schematic and partially cut-away view of a dental furnace according to the invention.

The dental furnace 10 illustrated in FIG. 1 has a furnace hood 12, which is mounted on a furnace lower part 16 by means of a pivoting articulated joint 14. The lower part 16 has on its top side a bearing surface 18, which is intended for receiving the dental material to be fired. A firing chamber 20 is provided in the furnace hood 12, and it extends in the manner of a rather flat cylinder and, with the furnace hood 12 closed, is closed off at the bottom by the bearing surface 18, such that the bearing surface 18 forms the bottom of the firing chamber 20.

The firing chamber 20 is surrounded annularly or spirally by heating elements 22.

According to the invention, particularly powerful heating elements are provided, which are designed such that they are fundamentally able to heat up the furnace from room temperature to 1600° C. within approximately a quarter of an hour. The dental furnace accordingly has a max. temperature gradient of 120° K/min.

The heat capacity of the firing chamber 20 and of the parts surrounding the firing chamber 20 is low.

The heating elements 22 are additionally significantly rear-ventilated. An air space 28 is provided for this purpose, said air space surrounding the heating elements 22 and thus the firing space 20 on all sides. The air space 28 is extremely large and takes up a considerable part of the interior of the furnace hood 12. The furnace hood 12 has a thermal insulation layer 30 surrounding the air space 28, which layer—even though this cannot be seen in FIG. 1—can also have perforations forming air ducts in order to facilitate the air flow via air outlets 32 in the upper region of the furnace hood 12.

The dimensioning both of the air space 12 and of the thermal insulation layer 30, can be adapted to the requirements within wide ranges, it also being possible to work with an extremely thin thermal insulation layer of just 15 mm, for example.

The dental material preferably provided is applied to the bearing surface 18 according to the invention. After the furnace hood 12 has been closed, the heating element 22 is switched on with maximum power, such that the firing chamber 20 is heated extremely rapidly to 1200° C., for example. This temperature may substantially correspond to the presintering temperature. After this, during an intermediate heating period, the temperature is increased with a small temperature gradient until a temperature of approximately 100° C. below the final temperature has been reached. After this, the temperature is increased extremely rapidly again to the final temperature and after this is held for a predetermined time duration, wherein the holding time may depend both on the applied amount of dental material and on further parameters.

After this, the temperature is reduced, to be precise preferably firstly without active cooling, wherein the active cooling is switched on when the presintering temperature has been reached again, such that the cooling proceeds more rapidly starting from said temperature until room temperature is reached.

As an alternative, in an even more highly accelerated firing cycle, the cooling down can take place directly after the holding time with active cooling, such that the cooling-down period overall is shortened further.

An initial heating-up period 40, which is ended at approximately 1100° C. in accordance with curve 2, is followed by an intermediate heating period 42, which performs heating up to approximately 1350° C.

After this, an end heating-up period 44 is provided, which increases the temperature to 1500° C., which final temperature is reached 100 min after the beginning of the firing cycle in the case of "curve 2".

During the holding time 46 of approximately 30 min, the temperature is held at 1500° C. and, during the initial cooling-down period 48, the temperature is lowered to 1100° C. within less than 30 min.

After this, the end cooling period 50 is provided, by means of which the temperature is lowered to room temperature within likewise somewhat less than half an hour.

Figure 2:
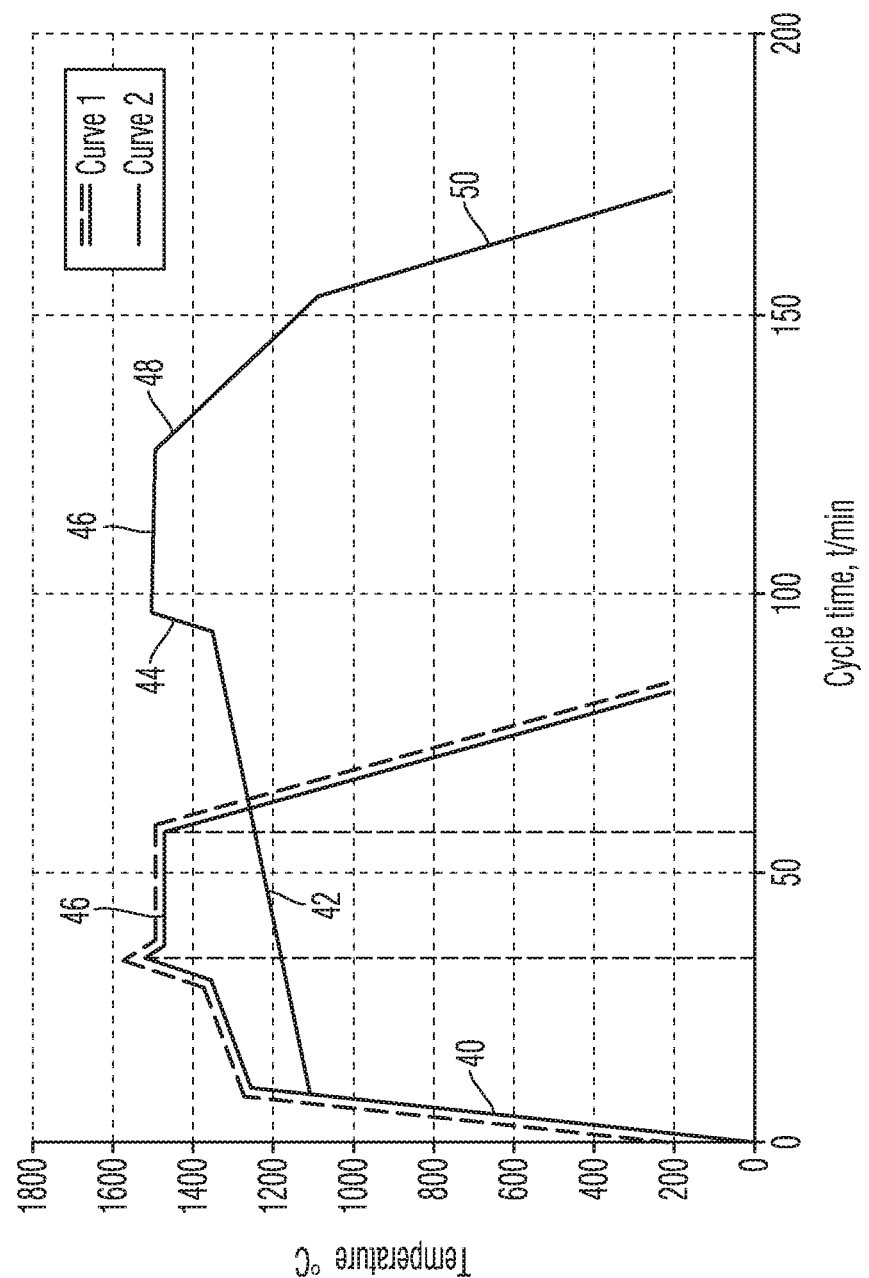
FIG. 2 shows two exemplary embodiments of firing curves for the dental furnace according to the invention.

This firing cycle according to the invention is illustrated in two embodiments in FIG. 2. Accordingly, the following firing curve results for the curve designated as "curve 2":

| Firing curve 2 | | | | |
|---|---|---|---|---|
| Ramp | Temperature/ C. | Rate/ K min$^{-1}$ | Time/ min | Total/ min |
| 0 | 25 | | | |
| 1 | 1100 | 100 | 10.75 | 10.75 |
| 2 | 1350 | 3 | 83.33 | 94.08 |
| 3 | 1500 | 50 | 3.00 | 97.08 |
| 4 | 1500 | 0 | 30.00 | 127.08 |
| 5 | 1100 | −15 | 26.67 | 153.75 |
| 6 | 200 | −50 | 18.00 | 171.75 |

| Firing curve 1 | | | | |
|---|---|---|---|---|
| Ramp | Temperature/ C. | Rate/ K min$^{-1}$ | Time/ min | Total/ min |
| 0 | 25 | | | |
| 1 | 1250 | 100 | 12.25 | 12.25 |
| 2 | 1350 | 5 | 20.00 | 32.25 |
| 3 | 1500 | 50 | 3.00 | 35.25 |
| 4 | 1500 | 0 | 25.00 | 60.25 |
| 5 | 1100 | −25 | 16.00 | 76.25 |
| 6 | 200 | −46.6 | 19.31 | 95.56 |

The total firing curve is reduced even further in the modified embodiment in accordance with "curve 1" to approximately 95 min, wherein a substantially trapezoidal curve profile is provided in both cases, each having a high initial heating-up rate and an equally or almost equally high end cooling-down rate. This is also evident from the table above.

In contrast to the firing cycle in accordance with curve 2, an overshoot of the heating power to a temperature of, for example, 50° C. above the temperature of the holding time 46 is provided in the case of curve 1.

Surprisingly, the strength is increased by the rapid heating-up to the presintering temperature, or alternatively to 1250° C., while there is no measurable influence on the accuracy of fit. By contrast, the accuracy of fit and hence the distortion are improved by the slow heating up during the intermediate heating period, while the strength is not adversely affected. By contrast, the end heating up, for example by 150° C., to the end heating up temperature, which may lie between 1500° C. and 1600° C., has no particular influence on the strength and no influence at all on the accuracy of fit.

By contrast, the comparatively long holding time has a very great influence on the strength and in particular also on the final density, and the relatively slow cooling-down to the presintering temperature as provided in accordance with curve 2 also has a measurable influence on the strength, while the subsequent cooling down to room temperature has practically no further influence on the strength or the density.

According to the invention, it is therefore possible to realize a dental furnace with a short firing cycle, yet particularly attractive firing results.

It is to be understood that different materials being used for the dental restoration parts (dental objects) require different sintering temperatures for an optimal firing result of the dental restoration parts.

However, in extensive research on the materials being used for making dental restoration parts it has further been found that the heating-up rates both of the first heating-up rate and the end heating-up rate are also strongly dependent from the material used for the dental restoration parts. Moreover, also the cooling rate for the forced cooling of the furnace after the firing cycle itself has been completed shall be adapted as being a function of the heating-up rates as mentioned before.

Figure 3:
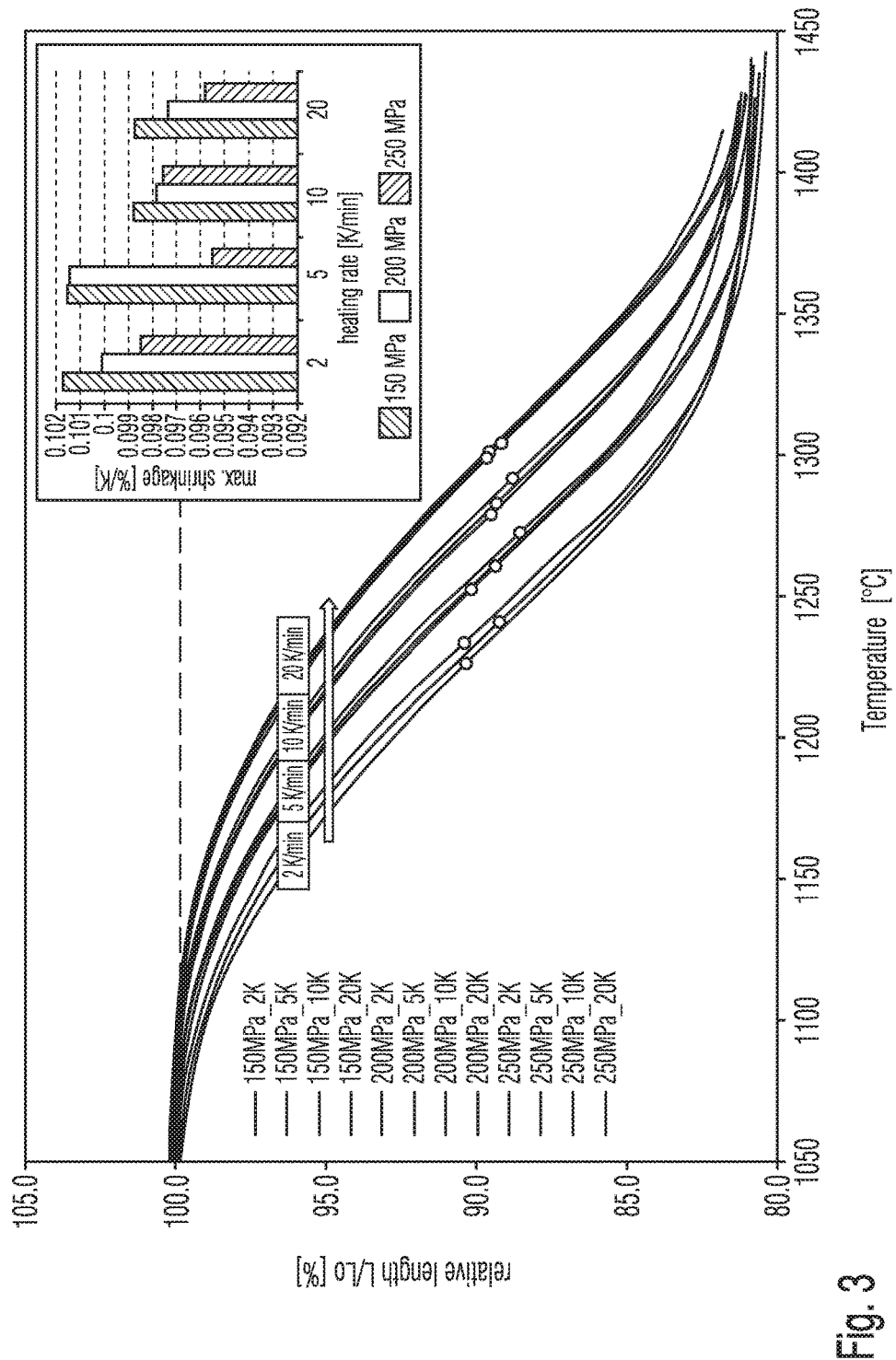
FIG. 3 shows the dependency of the shrinkage on different heating-up rates and as a function of different predensification.

FIG. 3 is showing the dependency of the shrinkage of the ceramic material from different heating-up rates and further as a function of different predensification of the ceramic material. Thus, the higher the heating-up rate of the ceramic material the higher the temperature can be for the same shrinking rate. The material which has been used for the research shown in FIG. 3 is with 3 mol-% $Y_2O_3$ partially stabilized zirconium oxide powder with a specific surface area of approximately 13 m$^2$/g.

It can be seen from the graphs shown in FIG. 3 that the sintering process, i.e. the enhanced diffusion at the grain boundaries of the ceramic material, is further dependent on the predensification by pressing or by powder compaction, respectively. The more the ceramic material is predensified the smaller is the temperature at which sintering of the ceramic material starts. This takes place in the range of approx. 1050° C. to approx. 1350° C. and is however strongly dependent from the material used.

Figure 4:
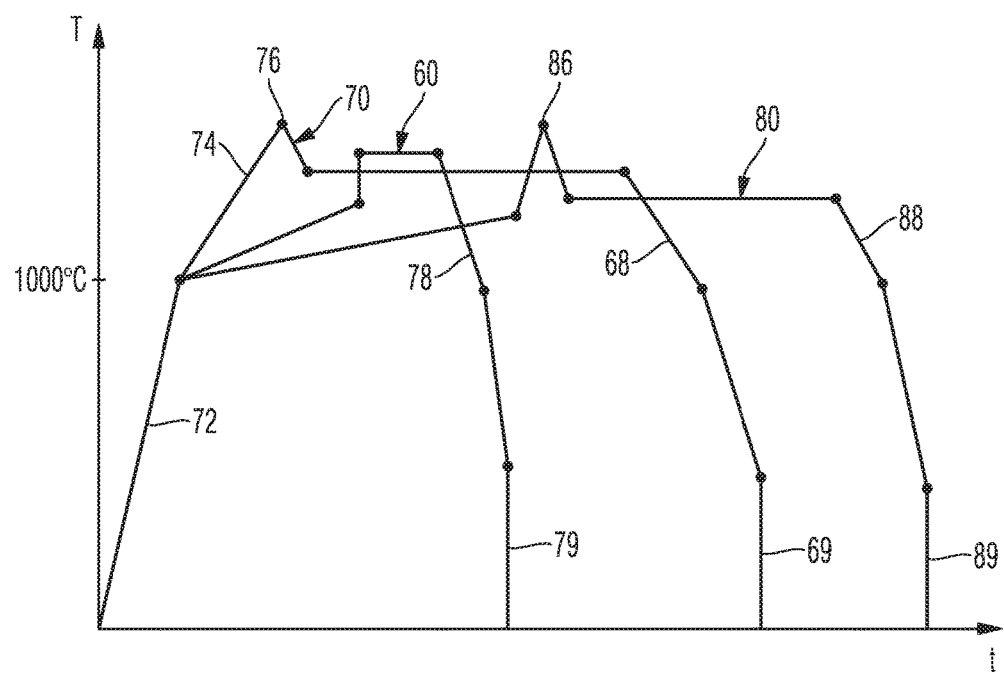
FIG. 4 shows temperature curves for firing cycles for different dental objects.

FIG. 4 illustrates three temperature curves as examples for different firing cycles being used for different designs (standard, monolithic crown, bridge) but for the same material. As can clearly be seen from FIG. 4 small restorations parts such as crowns (see graph 70) can be heated up much faster than dental bridges comprised of multiple artificial teeth (see graph 80). With graph 60 a standard heating curve is illustrated.

The sintering process in this above-mentioned temperature range shall take place at a heating-up rate which is lower than the first heating-up rate 72, in order to have equalized sintering of the dental object(s). This ensures low shrinking rate and high dimensional accuracy of the dental object(s). Little over-heat peaks (76, 86) can be seen in the graphs in FIG. 4 which further support high heating-up rates without exceeding the respective temperature of the dental object itself due to thermal inertia of the material sintered.

Furthermore, several materials such as oxide ceramics tend to exhibit grain growth at high temperatures. In order to reduce this undesired growth of the grains it is possible to only shortly raise the temperature up to a maximum value and then to reduce the temperature by approximately 50 to 100° C., in order to achieve a fine grained structure of the sintered ceramic material. This can also be seen from FIG. 4 with the graphs 70 and 80 around peaks 76 and 86, respectively.

The section 72 in FIG. 4 which is common for all three illustrated temperature curves according to graphs 60, 70, and 80 can be of any desired heating-up rate. This means that the dental furnace can even be pre-heated up to a desired temperature (e.g. 1,100° C.) prior to placing the dental restoration parts to be fired in the dental furnace. The preheat temperature of the dental furnaces shall be in the region of temperature where sintering would start for a specific ceramic material. When putting the dental objects to be fired into the firing chamber of the dental furnace the furnace temperature will normally decrease to a certain extent due to energy (heat) loss via the opened oven hood and further due to the heat capacity of the substantially cold dental objects, supports, etc.

However, due to the highly preheated dental furnace the rise of temperature of the dental objects itself will be significantly higher than the heating up rate of the dental furnace itself. The temperature curve of the dental objects will follow an e-function up to the preheat temperature of the dental furnace. Since the preheat temperature of the dental furnace is not higher than the temperature point where the sintering of the ceramic grains starts no undesired shrinking will occur to the dental objects.

The last sections of the three temperature curves 68, 78, and 88 show the cooling rates for the different dental objects. In the temperature range (for the specific material illustrated) down to approximately 1,100° C. a controlled forced cooling takes place which is adapted to the respective heating-up rates. For the further course of temperature, i.e. cooling down to room temperature, the cooling rate is quite uncritical, especially for the last sections 69, 79, and 89, respectively.

Figure 5:
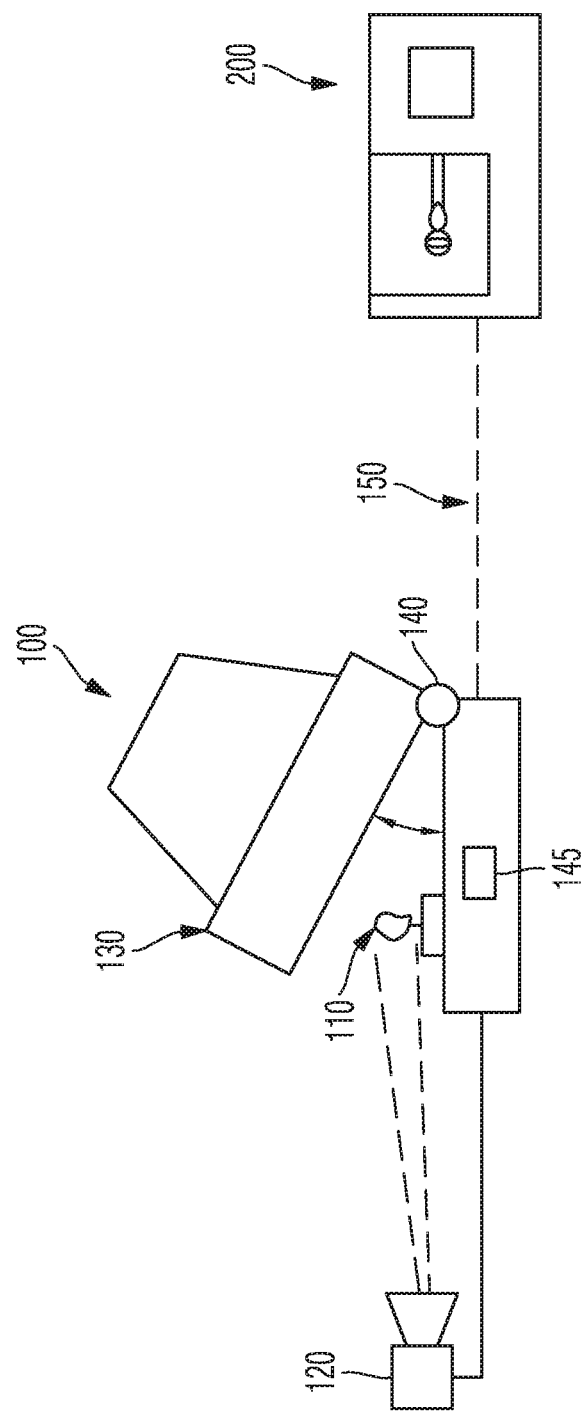
FIG. 5 shows a system with a furnace and machining device according to the invention.

In a preferred embodiment the dental furnace 100 is connected to a dental machining device 200 which is in particular a CNC (computerized numerical controlled) device e.g. a milling machine or generally referred to as a CAD/CAM device. An exemplary system is illustrated in FIG. 5. Usually computer controlled milling machines are used for manufacturing the dental objects which are to be sintered after finalizing the milling process. The 3D data for manufacturing the desired dental object are usually given as CAD (computer aided design) data representing dimensions and shape of the dental object.

The ceramic material which is not yet sintered ("green body") can quite easily being machined, e.g. milled. Cost effective devices for a so-called "side chair" production which can be realized even in the dentist's operatory "next to" the patient's chair are already available.

Thus, it is inventively also possible to connect the dental furnace 100 which is also present in the dentist's operatory with the dental machining device 200 for the purpose of exchanging parameters (or meta data, respectively) of the dental object to be made as well as control commands between the dental furnace and the dental machining device. This connection 150 can be made wired or wireless as well. LAN (local area network) which is usually always present at any place in present time as well as WiFi (wireless LAN) connections or any other common digital wireless data connection can be used to establish such a connection between the dental furnace 100 and the dental machining device 200.

Due to the fact that any shape and dimensional information of the dental object to be manufactured (as well as the material, density, etc.) will be present in the machining device (CAD data) for the milling process it is easily achievable to derive further information such as the mass (and thus the thermal capacity of the respective material) of the dental object to be made as well as basic conditions such as the fact whether the green body or blank shall be "wet" machined, i.e. if any liquid will be present for supporting the machining process. This information (herein called meta data) can then be transferred to the dental furnace 100 as a basis for selecting an appropriate firing program. Further to the material to be burned (which is vital for presetting the firing temperature range which is needed in general) further information such as the type of the dental restoration part (monolithic crown, veneer, bridge, etc.) and additional processing steps (glaze firing, etc.) can be provided from the machining device 200 to the dental furnace 100.

The dental furnace 100 in turn can provide information on how long the time span will be for pre-heating the dental furnace from room temperature up to a preset temperature. This time span is referred to as timing data. This can inventively make it possible to automatically start the pre-heating period of the dental furnace 100 such that the preset pre-heating temperature will be reached at the time the milling process of the ceramic green body will be finished.

With the thus determined time span for pre-heating the dental furnace 100 provided from the dental furnace the dental machining device 200 is able of initializing the pre-heating of the dental furnace by means of a control command which is sent from the machining device 200 to the dental furnace 100. The point of time for sending this control command can be derived by the machining device 200 using previously determined remaining machining time until finishing of the machining process taking into consideration the above-mentioned determined time for heating-up the dental furnace which has been provided by the dental furnace 100 via said digital data connection 150 between these two devices.

Manufacturing time which encompasses the milling time and the firing time of the dental object can significantly shortened.

By means of the above-mentioned pre-heating of the dental furnace the effective heating-up rate of the dental restoration part 110 itself can be much higher than the heating-up rate of the dental furnace. Since the dental furnace 100 itself has already reached the desired pre-heat temperature the dental object(s), which are inserted into the hot furnace in a cold state, can reach this pre-heat temperature much faster due to its/their little thermal capacity compared to the significantly higher thermal capacity of the dental furnace. The maximum achievable heating-up rate of the dental furnace is thus of quite little relevance for the first heating-up of the dental object(s) to be burned.

In order to further increase the heating-up rate of the dental objects it is also possible to shortly "over-heat" the furnace to a certain extent. While this short over-heating ("peak temperature") takes place only for a short time period the temperature of the dental object(s) will not exceed a material-specific maximum temperature and the dental objects will thus not be damaged by the "heat peak" of the dental furnace. However, the relevant temperature of the dental object(s) is thus reached faster compared to a furnace which only heats up to said (material-specific) maximum temperature.

The inventively high heating-up rate are obviously only applicable for the first heating-up rate, i.e. only in the temperature range up to the temperature where the grain boundaries of the ceramic material starts to melt. After this beginning of sintering (fusing the grains together) a second (slower) heating-up rate is required, in order to limit shrinking and dimensional deformation of the material as far as possible. Also, the quality of the sintered surface is much better with a low intermediate heating-up rate.

In an alternative embodiment it is possible to detect the size of the dental restoration part by means of an optical sensor, e.g. a video camera or IR camera which is shown in FIG. 5. Controlling the firing parameters and selecting an appropriate firing program can also be achieved based on this optical detection of the dental restoration part(s).

In a further preferred embodiment the dental furnace can be used for drying the green body or blank of the dental object 110 to be made if necessary. Based on the meta data provided by the dental machining device 200 the meta data also comprising information whether the dental object has e.g. been machined using liquids (as already mentioned above, for cooling or for supporting the machining process, as well as to flush the removed material away from the dental object during the machining process) or if the dental object 110 needs drying prior to the firing process in any way, the inventive dental furnace 100 can be utilized to achieve this drying of the dental objects(s) as well.

In order to dry a dental object 110 the oven hood 130 of the inventive dental furnace 100 comprising the heating means (rods or coils) is pre-heated to temperatures in the range of around 450° C. In order to limit the temperature for the dental object to be dried to a maximum allowable temperature the oven hood 130 is inventively partially opened. The effective surface temperature of the dental objects to be dried, according to the material used for the dental object(s), can start at approx. 70° and must not exceed 140° C., in order to avoid damaging the green body. It turned out in extensive research that the angle of aperture of the oven hood 130 is best in the range around 55% aperture of the ovenhood, where 0% aperture refers to the completely closed oven hood and 100% aperture refers to the maximum opening of the oven hood 130. This is also illustrated in FIG. 5.

Taking into account the aforesaid, it is understood that the quick heating-up to temperatures up to 1,100° C. which is mentioned further above cannot be applied in the case that drying of the dental object(s) must take place prior to sintering thereof.

According to this preferred embodiment, in order to achieve a constant drying temperature, it is either possible to continuously adjust the angle of aperture of the oven hood 130 or to leave the angle of aperture at a constant value (e.g. 55%) and to continuously adjust the energy supplied to the heating of the dental furnace, or a combination of both adjusting angle of aperture and heating power. In order to provide automatic operation, the oven hood 130 is driven by a motor 140 whereas the motor 140 is controlled by the control device 145 of the dental furnace 100. A suitable temperature detection element is connected to the control device 145 which allows the control device 145 to adjust the angle of aperture of the oven hood or the heating energy provided, respectively, in order to control the drying temperature to the desired value.

In a still further preferred embodiment of the invention an IR camera is connected to the control device of the dental furnace which is capable of detecting the temperature of the dental object(s) to be dried. The IR camera is inventively arranged outside the firing chamber of the dental furnace and the detection range of which is directed to the dental object(s) being placed on the oven base of the dental furnace which is also illustrated in FIG. 5. Since the oven hood 130 (during drying operation mode) is in a partially opened state the IR camera 120 is capable of monitoring the temperature of the dental object(s) during the drying process.

By means of monitoring the course of temperature detected by the IR camera 120 it is possible to detect the temperature at which the liquids contained in the dental objects 110 evaporate. This is disclosed in application number US 2014/0231408 A, which is hereby incorporated by reference.

In an alternative embodiment the temperature of the object(s) to be dried is not detected by means of an IR camera which means that the IR camera is not needed which can help to save costs of the dental furnace. In contrast to the afore-mentioned embodiment, the temperature control is achieved by means of special drying program modes which will set e.g. the angle of aperture of the oven hood, the energy supplied to the furnace heating, and the time span for drying the dental object(s) based on the meta data provided from the machining device connected to the furnace. Based e.g. on the material, the mass and the number of dental object(s) to be dried, the control device of the dental furnace is capable of determining the heat and time needed to completely dry the dental object(s), i.e. to evaporate any moisture, binders, etc. contained in the dental objects.

It is understood that extensive research has been made with the respective materials of dental objects, in order to create the drying program routines for the dental furnace such that it will be reliably possible to control the drying temperature within the inventive dental furnace without the need of an IR camera.

It should be noted that incomplete drying the dental object(s) can cause severe damage to the dental object(s) when rapid heating of the dental furnace will be applied subsequently. In order to ensure complete drying of the dental objects(s) a certain time span (in the range of several minutes) can be added to the drying-cycle time as a security buffer time after termination of the drying-cycle determined by the control device.

Beyond the aspect of saving costs the above alternative embodiment can also ease the handling of the dental furnace. For instance, it will not be necessary to take care whether warm or hot objects adjacent to the dental furnace will be present which would be capable of interfering the temperature measurement being made with the IR camera. Thus it is possible, that this alternative embodiment can help to improve the simple handling of the dental furnace or to make the temperature control more robust compared to the embodiment comprising an IR camera.

Generally speaking, it is one essential feature of the invention to reduce the number of operation steps needed to be made by the operating person, e.g. the dentist or the technician, to the lowest extent possible.

It is understood that the embodiment comprising the IR camera will provide for a best-optimized drying-cycle time since the time when the object(s) will completely be dried can be detected safely and quick. The firing cycle for sintering the dental object(s) can thus be started immediately after the detection of the completed drying-cycle. Therefore, the oven hood is closed completely and the furnace heating will be provided with maximum power to achieve high heating-up rates as being mentioned further above.

However, it can also be favorable to accept a drying-cycle time which is (in the worst case) several minutes longer but a more cost-efficient furnace can be used in combination with a simplified operation. With respect to the already mentioned chair-side production in a dentist's operatory this simplified operation may be of greater importance than saving little time for manufacturing the dental object(s).

Contrary to this, in large dental laboratories saving time may be more vital, in order to increase the production output. Usually, the operators of the dental furnaces in dental laboratories are more experienced in operating the furnaces and will thus be able to take better care of the operation conditions (such as heat sources in the detection range of the IR camera or temperature detection means, respectively, which would interfere with the temperature detection, or frequent cleaning of sensors and cameras, etc.). These are issues a common dentist or assistant should not be burdened with.

For the common dentist's operatory it will be of much greater importance to have drying and firing of the dental object(s) in one single device and further to operate it with minimum effort. Costs and space (for putting a second device, e.g. a drying cabinet) can thus be saved. Furthermore, the dentist is less distracted from his or her actual business and is able to better satisfy client's needs without having to accept minor quality of the dental object(s).

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the terms as used in the claims are intended to include not only the designs illustrated in the drawings of this application and the equivalent designs discussed in the text, but are also intended to cover other equivalents now known to those skilled in the art, or those equivalents which may become known to those skilled in the art in the future.

What is claimed is:

1. A system comprising
   a dental machining device for manufacturing at least one dental object and
   a dental furnace for sintering the at least one dental object;
   wherein the dental machining device and the dental furnace are connected to each other via a digital data connection comprising a wired or wireless data connection;
   wherein the dental machining device provides data of the at least one dental object which is to be manufactured in said dental machining device prior to sintering the at least one dental object in the dental furnace;
   wherein the data provided by the dental machining device comprise at least meta data of the at least one dental object to be manufactured by the dental machining device; and
   wherein control commands are exchanged between the dental machining device and the dental furnace.

2. The system according to claim 1, wherein the dental machining device comprises a CAD/CAM (computer-aided design/computer-aided machining) device.

3. The system according to claim 1 wherein the at least meta data to be provided by the dental machining device comprise further information of a material of the at least one dental object sintered.

4. The system according to claim 1 wherein the at least meta data to be provided by the dental machining device comprise further information of a mass of the at least one dental object sintered.

5. The system according to claim 1 wherein the at least meta data to be provided by the dental machining device comprise further information of the type of the at least one dental object sintered.

6. The system according to claim 5 wherein the further information of the type of the at least one dental object comprises a veneer, a crown, or a bridge.

7. The system according to claim 1 wherein the at least meta data to be provided from the dental machining device comprise further information of how many dental objects are to be sintered together in one firing cycle of the dental furnace.

8. The system according to claim 1 wherein the at least meta data to be provided from the dental machining device comprise further information of whether single or multiple firing cycles are needed to sinter the at least one dental object.

9. The system according to claim 1 wherein a control device of the dental machining device determines a remaining machining time for manufacturing the at least one dental object based on the at least meta data of the at least one dental object be to manufactured, and initiates a pre-heating of the dental furnace based on a determined remaining machining time.

10. The system according to claim 1 wherein the dental furnace further comprises a control device and wherein the dental furnace is preset to a desired pre-heating temperature; and
    wherein the control device of the dental furnace determines a time span needed for pre-heating the dental furnace up to a preset pre-heat temperature, and
    wherein the dental furnace provides said determined time span for pre-heating the dental furnace up to the preset pre-heat temperature as timing data to the dental machining device.

11. The system according to claim 1 wherein the at least meta data to be provided from the dental machining device comprise further information of whether drying of the at least one dental object is necessary or not prior to sintering.

12. The system according to claim 1 further comprising an oven hood being pivotably mounted to an oven base of the dental furnace and wherein the oven hood can be pivoted by means of an oven hood driving means, in order to adjust an angle of aperture of the oven hood, and
    wherein the dental furnace is operated in a drying operation mode prior to sintering of the at least one dental object based on the at least meta data provided, and
    wherein drying of the at least one dental object is obtained by applying heat from the pre-heated said dental furnace while the oven hood is in an at least partially opened state.

13. The system according to claim 12 wherein the angle of aperture of the oven hood is continuously controlled by a control device of the dental furnace, in order to adjust a temperature of the at least one dental object to be dried to a desired optimum temperature and to hold the temperature during drying of the at least one dental object based on the at least meta data provided.

14. The system according to claim 12 wherein the angle of aperture of the oven hood is set to a fixed value by a control device of the dental furnace, and wherein the temperature of the at least one dental object to be dried is controlled by accordingly controlling heat energy provided by heating, in order to obtain and to hold a desired optimum temperature during drying of the at least one dental object based on the at least meta data provided.

15. The system according to claim 12 wherein the system further comprises a temperature detection means arranged outside the heating chamber of the dental furnace wherein a detection range of the temperature detection means is directed toward the heating chamber and wherein the temperature detection means is capable of a temperature detection of the at least one dental object when the oven hood is in an at least partially opened state.

16. The system according to claim 15 wherein the temperature detection means is coupled to a control device of the dental furnace and
   wherein the control device is capable of detecting a completion of the drying process of the at least one dental object based on temperature values provided from the temperature detection means, and
   wherein the control device automatically starts the sintering of the at least one dental object after said detection of the completed drying process, in particular after completely closing the oven hood.

17. The system according to claim 1 wherein the dental furnace comprises
   a heating chamber heated up by at least one form of heating component comprising resistant heating, IR heating, induction heating, spark plasma sintering, pulsed electric current sintering or a combination thereof, wherein the dental furnace is configured such that
   the heating chamber is heated up in a first heating-up period at a first heating-up rate of more than 35° K/min, which heats the dental furnace to at least 1000° C.,
   wherein the first heating-up period is followed by an intermediate heating period, which is at least five minutes long,
   wherein the intermediate heating period is followed by an end heating-up period during which heating up is effected at a heating-up rate of more than 30° K/min, and wherein the end heating-up period is followed by a hold period in which a temperature of the dental furnace is held for at least five minutes above a temperature reached toward an end of the first heating-up period, and wherein forced cooling of the dental furnace is performed after the hold period,
   wherein gradients or heating-up rates both of said first heating-up period and an end heating-up rate are each adapted to a material to be sintered in the dental furnace, and
   wherein the forced cooling of the dental furnace takes place at a cooling rate which is based on both the rates of the first heating-up period and the end heating-up rate.

18. The system according to claim 17
   wherein the first heating-up rate is more than 100° K/min, which heats the dental furnace to more than 1100° C.,
   wherein the intermediate heating period is at least five minutes long,
   wherein the end heating-up period is effected at a heating-up rate of more than 50° K/min, and wherein the end heating-up period is followed by a hold period which is at least 25 minutes long,
   wherein the gradients or heating-up rates both of said first heating-up period and said end heating-up rate are each adapted to a physical mass and/or dimensions of the dental object to be sintered in the dental furnace.

19. The system according to claim 17
   wherein the intermediate heating period is at least ten minutes long.

* * * * *